United States Patent [19]

Scearce

[11] 4,369,655
[45] Jan. 25, 1983

[54] METHOD OF DETERMINING THE CONCENTRATION OF SOLID LUBRICANTS IN DRILLING FLUIDS

[75] Inventor: Forest A. Scearce, Houston, Tex.

[73] Assignee: NL Industries, Inc., New York, N.Y.

[21] Appl. No.: 215,677

[22] Filed: Dec. 12, 1980

[51] Int. Cl.³ .............................................. E21B 47/00
[52] U.S. Cl. .......................................... 73/153; 73/64
[58] Field of Search .................... 73/153, 61.4, 64; 175/65

[56] References Cited

U.S. PATENT DOCUMENTS 4,063,603 12/1977 Rayborn ................................. 175/65
4,269,279 5/1981 House .................................... 175/65 X Primary Examiner—Jerry W. Myracle
Attorney, Agent, or Firm—Browning, Bushman, Zamecki & Anderson

[57] ABSTRACT

A method of determining the concentration of spherical solids used as lubricants in drilling fluids in which the solid lubricant together with other solids of a given particle size are separated from a predetermined volume of the drilling mud, are admixed with a liquid, transferred to a graduated measuring tube which permits a direct reading of the volume of the solid lubricant.

13 Claims, 3 Drawing Figures

METHOD OF DETERMINING THE CONCENTRATION OF SOLID LUBRICANTS IN DRILLING FLUIDS

BACKGROUND OF THE INVENTION

The present invention relates to a method of determining the concentration of spherical solids used as lubricants in a drilling fluid.

U.S. Pat. No. 4,063,603 to Rayborn discloses a method of borehole drilling in which the drilling fluid or mud contains spherical plastic beads which are used to reduce friction between the drill string and the well bore and thereby reduce the amount of torque required to rotate the drill string during the drilling process. As is pointed out in the cited patent, in certain cases, the addition of the plastic beads beyond a certain amount does not materially reduce the torque required to rotate the drill string. Accordingly, a method of determining the concentration of the plastic beads in the drilling mud is desirable to ensure that the optimum amount of such beads is used.

SUMMARY OF THE INVENTION

It is therefore an object of the present invention to provide a method for determining the concentration of a solid lubricant used in a drilling fluid.

Another object of the present invention is to provide a method of determining the concentration of spherical plastic beads used as an additive in a drilling fluid to reduce the amount of torque required to rotate the drill string.

The above and other objects of the present invention will become apparent from the description given herein and the appended claims.

In one embodiment of the present invention a given volume of the drilling fluid or mud is admixed with a predetermined amount of liquid such as water. The mixture is agitated and passed through a sieve having a smaller mesh size than the spherical solids used as the lubricant in the drilling fluid. The spherical solids plus any other solids retained on the sieve are admixed with a wetting agent for the spherical solids. The wetting agent serves to ensure settling out of the spherical solids from the drilling fluid and thereby permits a determination of the volume of spherical solids present in the given volume of drilling mud originally sampled. This in turn can be easily related to the concentration of the spherical solids in the drilling mud being sampled.

In another embodiment of the present invention and when the drilling fluid contains materials having densities similar, but slightly less than that of the spherical solids, the method as described above is first carried out with the exception that the total amount of spherical beads and solids retained on the sieve is determined. The method is then repeated with the exception that instead of a wetting agent, the mixture of spherical solids and other solids retained on the sieve is mixed with a liquid solution having a density greater than that of the spherical solid. This causes the spherical solids to float while permitting the remaining solids to settle. By taking the difference between the volume of settled solids less the floating spherical solids and the total combined volume of settled solids and spherical solids, the volume of the spherical solids in the drilling fluid is then obtained.

DESCRIPTION OF THE PREFERRED EMBODIMENTS

Figure 1:
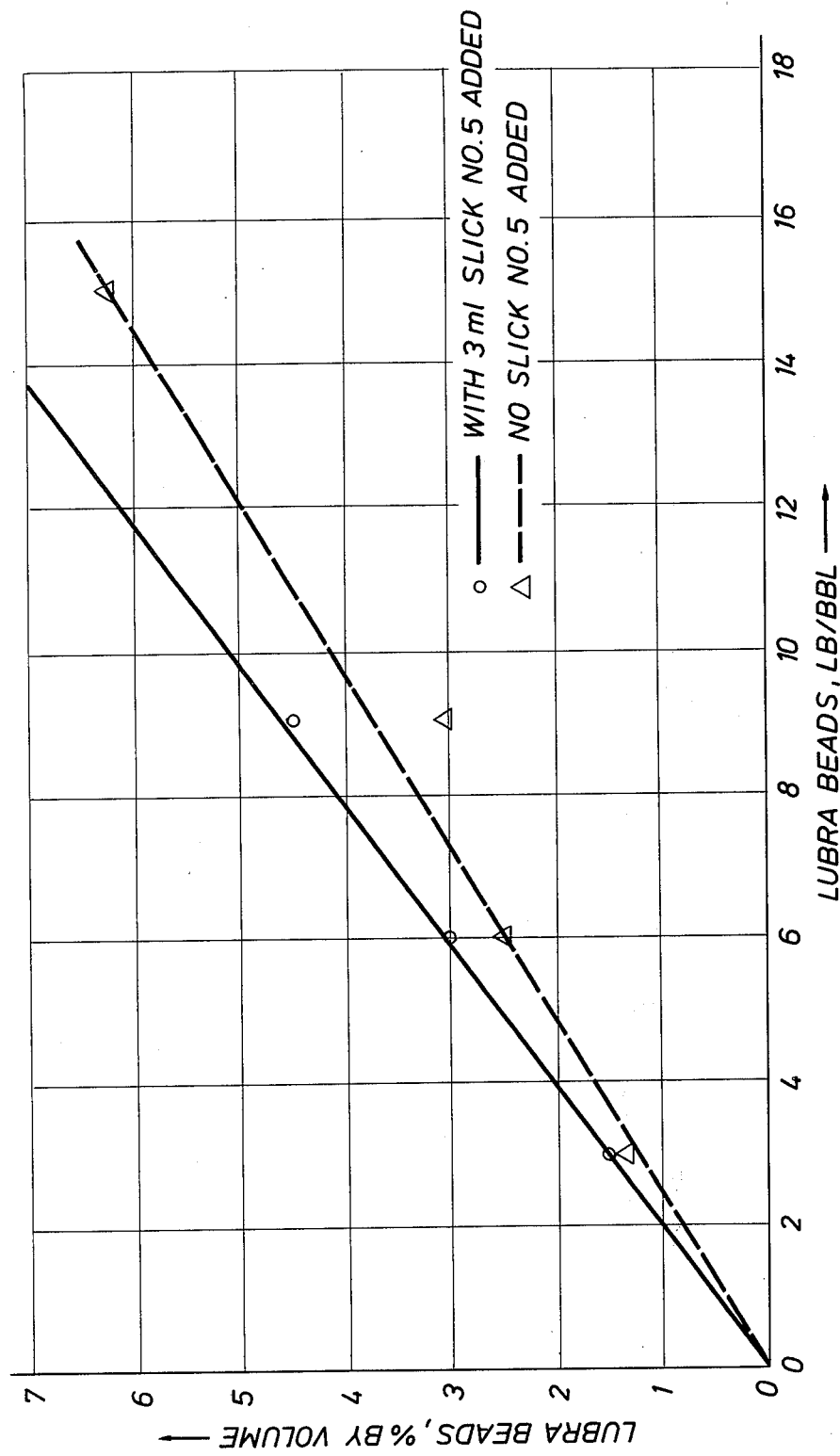
FIGS. 1, 2 and 3 are graphical representations of the data obtained using the method of the present invention.

As noted in aforementioned U.S. Pat. No. 4,063,603, incorporated herein by reference for all purposes, the plastic beads added to the drilling mud to act as a lubricant to reduce the torque required to rotate the drill string preferably have a chemical composition and polymeric structure such that they will not crush in actual operation in the well. The spherical, plastic beads are solid, insoluble in oil and water, stable at bottom hole temperatures ranging up to, for example, 250° F., are inert, both chemically and physically, to well fluids and generally have a specific gravity within the range of 1.1 to 1.5. As further pointed out in the aforementioned patent, the beads preferably should have a substantially perfectly spherical shape to provide maximum torque reduction. Although beads made of other polymeric materials work satisfactorily, beads made of a copolymer of divinyl benzene and styrene have been found to be especially useful. One form of such beads are known as LUBRA-BEADS (marketed by NL Baroid, Houston, Texas).

Since the spherical plastic beads or solids used are relatively expensive, and since beyond a certain concentration their effect in reducing torque is negligible or at least offset by the increased cost of using excessive amounts of beads, it is desirable that the concentration of the spherical solids in the drilling mud be monitored. As is well known to those skilled in the art, drilling mud can contain many additives such as weighting agents, viscosifying agents, etc. It is also known that as the drilling continues, the drilling mud becomes contaminated with sand and other cuttings from the borehole. Generally speaking the sand and cuttings are heavier than the spherical solids. However, in certain cases it is known that solids of relatively low density e.g. lignite, are present in the drilling muds, the lignite acting as a fluid loss additive. The present invention provides a method whereby the content of the spherical solids in the drilling fluid can be determined (a) when the drilling fluid contains only the spherical solids or solids which are considerably more dense than the spherical solids, and (b) when the drilling fluid contains, in addition, solids which are less dense than the sand normally found in the drilling fluid but more dense than the spherical solids employed as the lubricant.

The method of the present invention employs a sand content kit such as that used in SECTION 4, SAND of API RP 13B: Standard Procedure for Testing Drilling Fluids, incorporated herein by reference for all purposes. The sand kit in question consists of a 200 mesh sieve, a funnel to fit the sieve and a graduated glass measuring tube. The measuring tube is such that the percentage of sand (solids) settled in the bottom of the tube can be read directly.

In the method of the present invention and when only the spherical polymeric solids or the spherical polymeric solids and solids heavier than the spherical solids are present, a given amount of the drilling mud is added to the glass measuring tube followed by the addition of a predetermined amount of a liquid such as water. The mixture is then agitated and poured through the sieve, the liquid passing through the sieve being discarded.

Generally, the solids retained on the sieve are washed until water passing through the sieve is clear and essentially free of any solids. A wetting agent is then added to the measuring tube and solids retained on the sieve are washed, as with water, through the funnel into the measuring tube to be admixed with the wetting agent. The solids are allowed to settle and from the graduations on the tube the volume percent of the solids is determined. In the case where the drilling mud is free of solids other than the spherical solids or contains spherical solids and materials such as sand which is considerably heavier than the spherical solids, a good demarcation line exists between the heavier solids and the spherical solids such that the difference between the heavier solids and the spherical solids can be read directly from the graduated measuring tube to determine the volume of spherical solids. From a suitable calibration curve, the volume of spherical solids can then be converted to pounds of spherical solids per barrel in the drilling fluid.

As noted, it is not uncommon for the drilling fluid to contain, in addition to heavier solids and the spherical solids, materials such as lignite which are lighter than the spherical solids. These lighter materials e.g. lignite, are added to the drilling fluid as fluid loss control additives. In such cases, to determine the amount of spherical solids in the drilling fluid a two-fold method is employed. First, the total amount of settled solids is determined as per the method outlined above. Following this, the same procedure is carried out with the exception that instead of a wetting agent being admixed with the solids retained on the sieve, a liquid solution having a density greater than that of the spherical solids is admixed with the solids retained on the sieve. This causes the spherical solids to float in the liquid solution leaving only the heavier materials settled in the measuring tube. By taking the difference between the total volume of settled solids obtained initially and the volume of settled solids obtained in the second phase of the method, the total volume of spherical solids contained in the given volume of drilling fluid can be determined. This can then, from a suitable calibration curve, be converted to pounds of a spherical solids per barrel of drilling fluid.

Although the liquid commonly used to wash the solids retained on the sieve into the measuring tube is generally water, it is possible to employ other liquids which have the proper specific gravity. Thus, for example, aliphatic alcohols and the like having specific gravities near that of water can be employed.

The wetting agent can be any liquid which will wet the surface of the spherical solids sufficient to permit them to settle in a washed liquid of lower specific gravity than the spherical solids and which is inert. The wetting agent frees the spherical solids of air bubbles which cling to the spherical solids, making them buoyant and preventing them from settling out of the liquid. Generally speaking the wetting agent will be some surface active agent or surfactant which is capable of wetting a synthetic polymeric material. A particularly desirable wetting agent known as SLICK NO. 5 (marketed by NL Baroid, Houston, Texas) is a mixture of isobutyl Cellosolve, oxyalkylated nonyl phenol and alkanolamide. In the method of the present invention using the sand content test kit specified above, three ml. of wetting agent is employed. It will be understood however, that if different volume measuring tubes are employed and different volumes of drilling fluid are being tested, more or less of the wetting agent may be employed.

As noted above, in cases where the drilling fluid contains solids which are near the density of the spherical solids, it is necessary to utilize a two-fold procedure and in the second phase of the procedure to use a liquid solution which has a density greater than that of the spherical solids such that the sperical solids will float in the liquid solution and allow the heavier solids to settle out. It is only necessary that the liquid solution have a specific gravity greater than that of the spherical solids and be generally inert in that it does not react with the spherical solids. Suitable liquid solutions include aqueous salt solutions such as for example saturated sodium chloride solutions or saturated salt solutions of other alkali metals as for example, sodium bromide, potassium bromide, etc.

To more fully illustrate the present invention, the following non-limiting examples are presented: In all cases, the sand-content set used in RP 13B: Standard Procedure For Testing Drilling Fluids, Section 4, SAND was employed.

EXAMPLE 1

The concentration of LUBRA-BEADS in pounds/barrel (lb/bbl) versus percent volume was run at concentrations of 0, 3, 6, 9 and 15 lbs/bbl in clear water polymer mud. The glass measuring tube was filled to the indicated mark with the mud samples, water was added to the next mark, the mouth of the tube closed and vigorously shaken. The mixture was poured through the 200 mesh sieve, the liquid passing through being discarded. The tube was washed until only the beads remained on the 200 mesh screen. The funnel was fitted upside down over the top of the screen and the funnel and sieve slowly inverted, the tip of the funnel being placed into the mouth of the glass tube. The spherical beads on the screen were washed into the tube with water. It was noted that after 10 minutes, a small amount of LUBRA-BEADS continued to float in the water solution. In a second run, three ml. of SLICK No. 5 was added to the measuring tube before the LUBRA-BEADS were washed from the 200 mesh screen into the tube. Within five minutes it was noted that all the LUBRA-BEADS had settled and the volume thereof could be read directly from the graduated tube. The results are graphically depicted in FIG. 1. It can be seen that by using the wetting agent, a much better straight line relationship with less scattering of data points is obtained.

EXAMPLE 2

Figure 2:
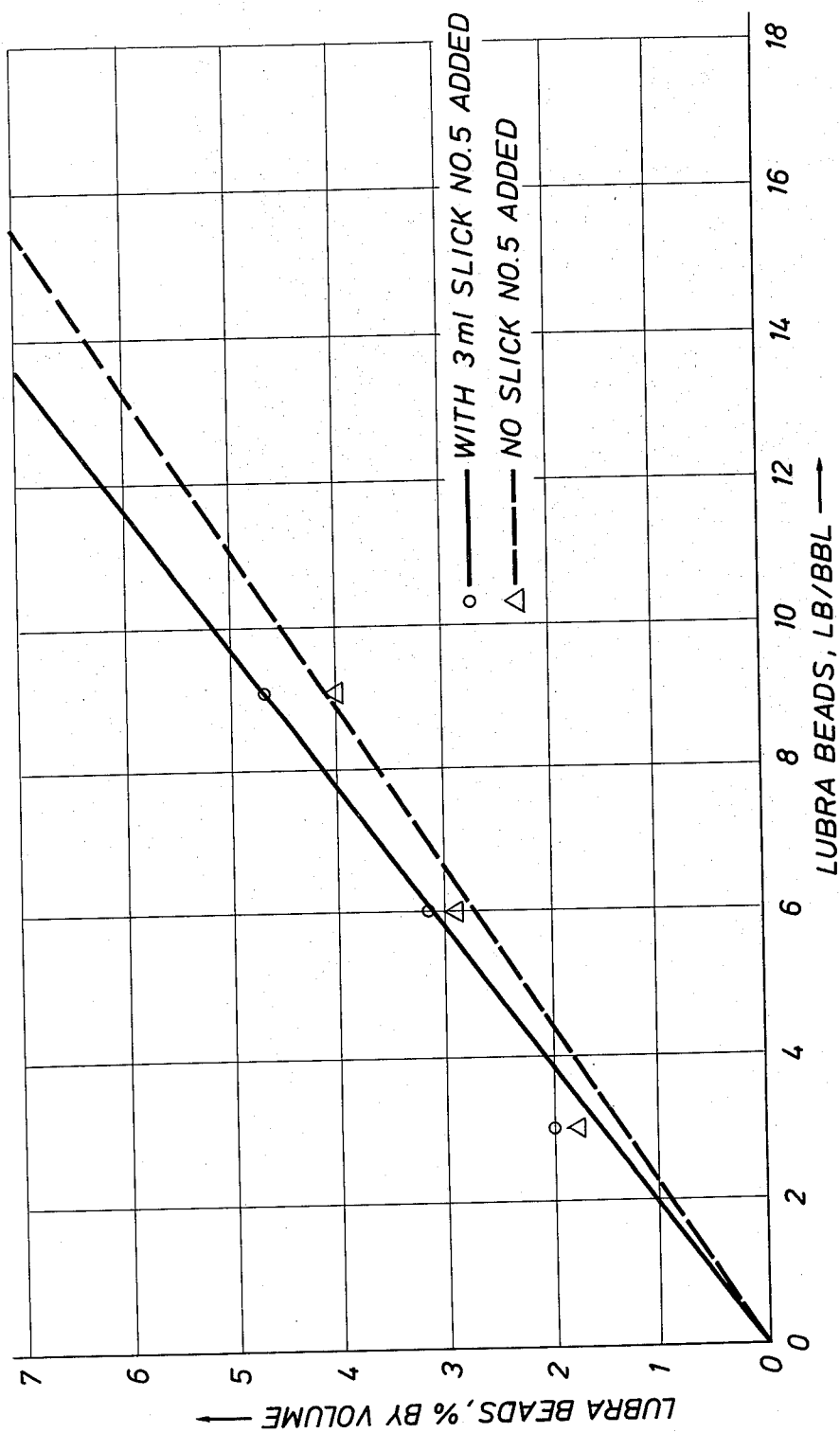

The procedure of Example 1 was followed using similar concentrations of LUBRA-BEADS in unweighted organic thinned mud containing 60 lb/bbl of Glen Rose shale. To determine the content of the LUBRA-BEADS, the difference between the total settled solids and the volume of darker heavier solids, solids at the lowermost portion of the tube was obtained. It was noted that at times there was no clear demarkation between the LUBRA-BEADS and the heavier solids such that it was difficult to obtain an accurate determination of the volume readings. Accordingly, the following procedure was carried out. The procedure of Example 1 was repeated (Run 1) and the total volume (LUBRA-BEADS plus heavier solids) of settled solids was obtained. The procedure of Example 1 was then followed on a second sample of the mud, except that saturated sodium chloride solution was used to wash the +200 mesh material into the graduated measuring tube (Run 2). No SLICK No. 5 was added. After agitation, the samples were allowed to set 5 to 10 minutes before reading the volume of heavier settled solids. It was noted that the LUBRA-BEADS floated in the saturated salt solution. The difference between the total volumes in Run 1 and Run 2 was taken as the volume of LUBRA-BEADS. The results are seen graphically in FIG. 2 where it can be observed that the two run method provides a better straight line relationship between the volume of LUBRA-BEADS determined and the actual lb/bbl content of LUBRA-BEADS in the drilling mud.

EXAMPLE 3

Figure 3:
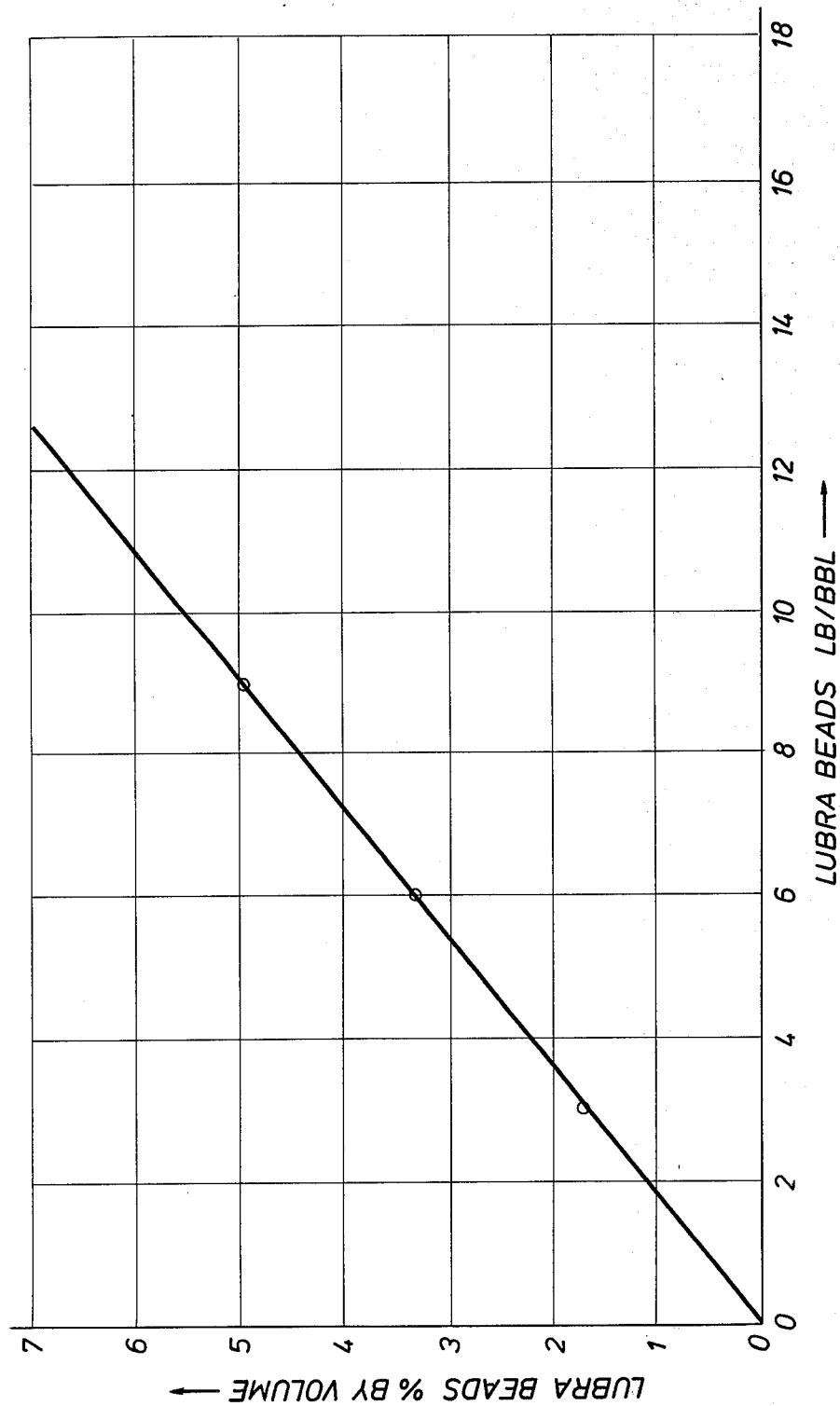

The two run procedure of Example 2 was followed to determine the volume of LUBRA-BEADS in a 15 lbs. per gallon organic thinned mud containing CARBONOX (Tradename of an organic humic acid material used to reduce viscosity and gel strength, and marketed by NL Baroid, Houston, Texas). It was noted that a small amount of the CARBONOX was retained on the 200 mesh screen but settled in the saturated salt water solution while the LUBRA-BEADS floated. The results are graphically demonstrated in FIG. 3 where it can be seen that an excellent straight line relationship between observed volume of LUBRA-BEADS and actual content of the LUBRA-BEADS in lbs/bbl is obtained.

The foregoing disclosure and description of the invention is illustrative and explanatory thereof, and various changes in the method steps may be made within the scope of the appended claims without departing from the spirit of the invention.

We claim:

1. A method for determining the concentration of spherical solids used as a lubricant in a drilling fluid comprising:
    (a) adding a liquid to a given volume of said drilling fluid;
    (b) agitating the mixture of said drilling fluid and said liquid;
    (c) passing the mixture of said drilling fluid and said liquid through a sieve of smaller mesh size than said spherical solids;
    (d) removing said spherical solids and any other solids from said sieve;
    (e) mixing said mixture of said spherical solids and said other solids with a wetting agent for said spherical solids;
    (f) permitting said mixture of said spherical solids and said other solids to settle in a graduated measuring means; and
    (g) determining the volume of said spherical solids contained in said given volume of said drilling fluid.

2. The method of claim 1 wherein said spherical solids have a density less than that of heavier solids present in said drilling fluid.

3. The method of claim 2 wherein said polymeric material comprises a copolymer of divinyl benzene and styrene.

4. The method of claim 1 wherein said spherical solids comprise a polymeric material.

5. The method of claim 1 wherein said sieve is a 200 mesh sieve.

6. The method of claim 1 wherein said liquid comprises water.

7. The method of claim 6 wherein said spherical solids comprise a polymeric material.

8. The method of claim 6 wherein said first and second liquids are the same.

9. The method of claim 6 wherein said sieve is a 200 mesh sieve.

10. The method of claim 6 wherein said liquid solution comprises a saturated salt solution.

11. A method for determining the concentration of spherical solids used as a lubricant in a drilling fluid, said spherical solids having a density intermediate that of other solids in said drilling fluid, comprising:
    (a) adding a first liquid to a first given volume of said drilling fluid;
    (b) agitating the mixture of said first given volume of said drilling fluid and said first liquid;
    (c) passing the mixture of said first given volume of said drilling fluid and said first liquid through a sieve of smaller mesh size than said spherical solids;
    (d) removing said spherical solids and said other solids from said sieve;
    (e) mixing said mixture of said spherical solids and said other solids with a wetting agent for said spherical solids;
    (f) permitting said mixture of said spherical solids and said other solids to settle in a graduated measuring means;
    (g) determining the total volume of settled solids contained in said first given volume of said drilling fluid;
    (h) adding a second liquid to a second given volume of said drilling fluid;
    (i) agitating the mixture of said second given volume of said drilling fluid and said second liquid;
    (j) passing the mixture of said second given volume of said drilling fluid and said second liquid through a sieve of smaller mesh size than said spherical solids;
    (k) removing said spherical solids and any other solids retained on said sieve;
    (l) mixing said spherical solids and said other solids from Step (k) with a liquid solution having a density greater than that of said spherical solids;
    (m) permitting said mixture of said spherical solids and said other solids to settle in a graduated measuring means;
    (n) determining the total volume of settled solids contained in said mixture of said other solids, said liquid solution and said spherical solids from Step (l);
    (o) determining the difference between the total volume of solids determined in Step (g) and the total volume of said settled solids determined in Step (n); and
    (p) determining the volume of said spherical solids contained in said second given volume of said drilling fluid.

12. The method of claim 11 wherein said polymeric material comprises a copolymer of divinyl benzene and styrene.

13. The method of claim 12 wherein said first and second liquids comprise water.

* * * * *